United States Patent
Graf et al.

(10) Patent No.: US 10,213,466 B2
(45) Date of Patent: Feb. 26, 2019

(54) METHODS OF USING LACTIC ACID BACTERIA AS PROBIOTIC STRAINS

(71) Applicant: PROBIOSWISS AG, Beckenreid NW (CH)

(72) Inventors: Federico Graf, Beckenreid (CH);
Philipp Grob, St. Gallen (CH);
Dominique Brassart, Chavannes/Renens (CH)

(73) Assignee: Probioswiss Ag, Beckenried NW (CH)

(*) Notice: Subject to any disclaimer, the term of this patent is extended or adjusted under 35 U.S.C. 154(b) by 48 days.

(21) Appl. No.: 15/291,880

(22) Filed: Oct. 12, 2016

(65) Prior Publication Data

US 2017/0027998 A1    Feb. 2, 2017

Related U.S. Application Data

(63) Continuation of application No. 11/577,680, filed as application No. PCT/EP2005/011152 on Oct. 17, 2005, now abandoned.

(30) Foreign Application Priority Data

Oct. 22, 2004  (WO) ............... PCT/EP2004/011980
Oct. 22, 2004  (WO) ............... PCT/EP2004/011981
Feb. 10, 2005  (WO) ............... PCT/EP2005/001354

(51) Int. Cl.
| | | |
|---|---|---|
| A61K 35/747 | (2015.01) | |
| A61K 9/00 | (2006.01) | |
| A61K 9/02 | (2006.01) | |
| A61K 9/48 | (2006.01) | |
| A61K 35/00 | (2006.01) | |
| A23L 2/38 | (2006.01) | |
| A23L 33/135 | (2016.01) | |
| C12R 1/225 | (2006.01) | |
| C12R 1/23 | (2006.01) | |

(52) U.S. Cl.
CPC .......... *A61K 35/747* (2013.01); *A23L 2/382* (2013.01); *A23L 33/135* (2016.08); *A61K 9/0034* (2013.01); *A61K 9/0053* (2013.01); *A61K 9/02* (2013.01); *A61K 9/48* (2013.01); *C12R 1/225* (2013.01); *C12R 1/23* (2013.01); *A23V 2002/00* (2013.01); *A61K 2035/115* (2013.01)

(58) Field of Classification Search
CPC .............. A61K 35/747; A61K 2300/00; A61K 2035/115; A61K 9/0034; A61K 9/0053; A61K 9/02; A61K 9/48; A23V 2200/00; A23V 2200/32; A23V 2200/3204; C12R 1/225; C12R 1/23; A23L 2/382; A23L 33/135
See application file for complete search history.

(56) References Cited

U.S. PATENT DOCUMENTS

| | | | |
|---|---|---|---|
| 5,176,911 | A | 1/1993 | Tosi et al. |
| 5,645,830 | A | 7/1997 | Reid et al. |
| 6,093,394 | A | 7/2000 | Chrisope et al. |
| 2003/0118571 | A1 | 6/2003 | Reid et al. |
| 2004/0071679 | A1 | 4/2004 | De Simone |

FOREIGN PATENT DOCUMENTS

| | | |
|---|---|---|
| EP | 0 956 858 A1 | 11/1999 |
| WO | WO 90/09398 A1 | 8/1990 |
| WO | WO 03/038068 A1 | 5/2003 |
| WO | WO 03/080813 A2 | 10/2003 |

OTHER PUBLICATIONS

Atassi, F. et al. 2006 "*Lactobacillus* strains isolated from the vaginal microbiota of healthy women inhibit *Prevotella bivia* and *Gardnerella vaginalis* in coculture and cell culture" *FEMS Immunol Med Microbiol* 48: 424-432.
Boris, et al. 1998; "Adherence of human vaginal factobacilli to vaginal epithelial cells and interaction with uropathogens" *Infection and Immunit, American Society for Microbiology* 66:1985-1989.
Database Biosis 'Online! Biosciences Information Service, (2004) Huang, C. et al. "Effects of Lactobacilli on the performance, diarrhea incidence, VFA concentration and gastrointestinal microbial flora of weaning pigs" XP002332656.
Database CA 'Online! Chemical Abstracts Service, (2003) Brassart, D. "L. acidophilus—NCFM: functional properties of a unique probiotic strain" XP002332655.
Database CA'Online! Chemical Abstracts Service, (1999) Michetti, P. et al. "Effect of whey-based culture supernatant of Lactobacillus acidophilus (johnsonii) La1 on helicobacter pylori infection in humans" XP002332657.
Granato, D. et al. (1999) "Cell surface-associated lipoteichoic acid acts as an adhesion factor for attachment of Lactobacillus johnsonii La1 to human enterocyte-like caco-2 cells" *Applied and Environmental Microbiology* 65:1071-1077.
Itoh, et al. 1995 "Inhibition of food-borne pathogenic bacteria by bacteriocins from Lactobacillus gasseri" *Letters in Applied Microbiology* 21: 137-141.

(Continued)

*Primary Examiner* — Deborah K Ware
(74) *Attorney, Agent, or Firm* — Knobbe, Martens Olson & Bear, LLP

(57) ABSTRACT

Useful probiotics have been selected among lactic acid bacteria strains of the genus *L. acidophilus*, *L. crispatus*, *L. gasseri*, *L. helveticus* and *L. jensenii* for their ability to kill urogenital and/or gastrointestinal pathogens and their ability to inhibit internalization of urogenital and/or gastrointestinal pathogens within urogenital and/or gastrointestinal epithelial cells in humans. Probiotic compositions comprise at least one of the said lactic acid bacteria strains in combination with a suitable delivery system, such as a food product or a beverage, a food or beverage compositions, a food or beverage supplement or adjuvant.

27 Claims, 1 Drawing Sheet

(56) References Cited

OTHER PUBLICATIONS

Mastromarino, et al. 2002 "Characterization and selection of vaginal Lactobacillus strains for the preparation of vaginal tablets" *Journal of Applied Microbiology* 93: 884-893.
Ocana, V. et al. (2001) "Adhesion of lactobacillus vaginal strains with probiotic properties to vaginal epithelial cells" *Biocell* 25: 265-273.
Pfeifer, A. et al. (1998) "Immunological effect of probiotic food" *Monatsschrift fur Kinderheilkune* 146: Suppl. 1:S13-S20.
Todoriki, K. et al. (2001) "Inhibition of adhesion of food-borne pathogens to caco-2 cells by Lactobacillus strains" Journal of Applied Microbiology 91:154-159.

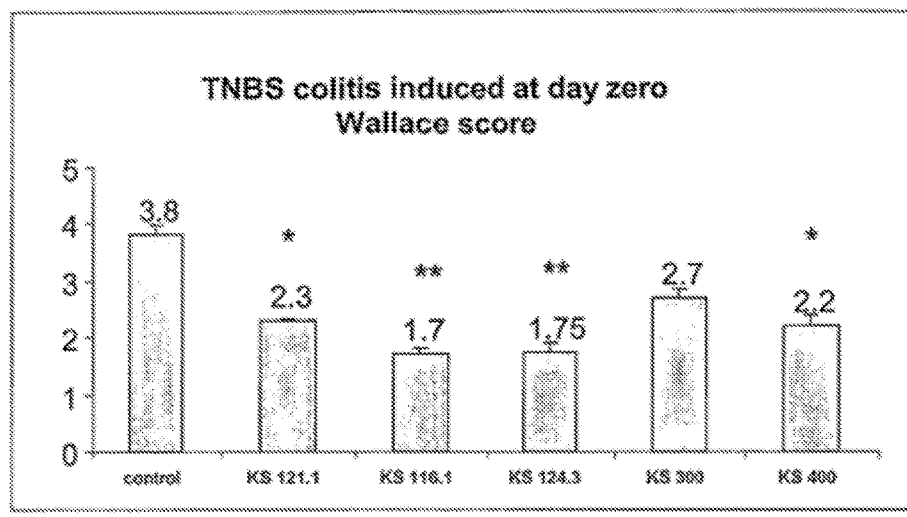
Table IV
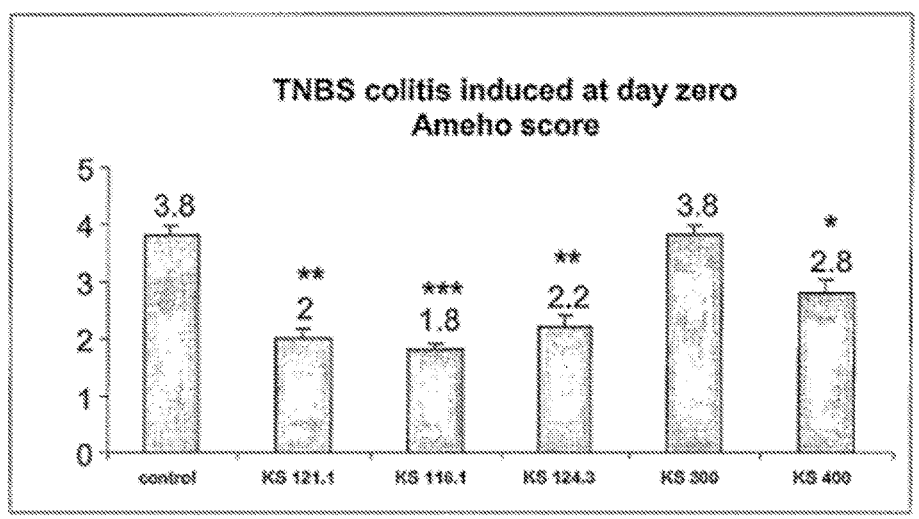
Table V

METHODS OF USING LACTIC ACID BACTERIA AS PROBIOTIC STRAINS

FIELD OF THE INVENTION

This invention refers to the use of new probiotic bacteria stains in the treatment of infectious troubles caused by various pathogens in mammals, more specifically the prevention and/or the treatment of urogenital and/or gastrointestinal infections in humans.

BACKGROUND OF THE INVENTION

Urogenital infections remain a common problem, particularly in the female population. Bacterial adherence to the urogenital epithelium is recognized as an important mechanism in the initiation and pathogenesis of urinary tract infections (UTI) and, in particular, of vaginal infections. The urogenital pathogens originate predominantly in the intestinal tract and initially colonize the per-urethral region and ascend into the bladder, resulting in symptomatic or asymptomatic bacterial uria. Alternatively, these bacteria invade and then colonize the vagina causing there various types of symptomatic as well as asymptomatic vaginal infections. Thereafter, depending on host factors and bacterial virulence factors, the organisms may further ascend and give rise to pyelonephritis, respectively ascending infections of the genital tract in women. Urogenital pathogens express virulence characteristics that enable them to resist the normally efficient host defence mechanisms.

The use of bacteria of the autochthonous flora, such as lactobacilli, to exclude urogenital pathogens from colonizing the urogenital tract is an established concept studied rather extensively since years (see e.g. Cadieux et al.—*Lactobacillus* strains and vaginal ecology—Jama. 287: 1940-41/2002; Butler B C, Beakley J W. Bacterial flora in vaginitis. Am J Obstet Gynaecol 1960; 78:432-40, Eschenbach D A, Davick P R, Williams B L, Klebanoff S J, Young-Smith K, Critchlow C M et al. Prevalence of hydrogen peroxide-producing *Lactobacillus* species in normal women and women with bacterial vaginosis. *J Clin Microbiol* 1989; 27:251-6, Sobel J D, Cook R L, Redondo-Lopez V. Lactobacilli: a role in controlling the vaginal microflora? in Horowitz B J, Mardh P-A, eds. *Vaginitis and Vaginosis*, pp 47-53. New York: Wiley-Liss, 1991, Lauritzen C, Graf F, Mucha M. Restoration of the physiological vaginal environment with Doederlein bacteria and estriol. *Frauenarzt* 1984; 4).

On the other hand gastro-intestinal infections remain a common problem in the human population. Bacterial adherence to the gastrointestinal epithelium has been recognized as an important mechanism in the initiation and pathogenesis of gastrointestinal tract infections (GH). Many gastrointestinal pathogens which colonize the intestinal tract may, depending on host factors and bacterial virulence factors, express virulence characteristics that enable them to resist the normally efficient host defence mechanisms.

The use of bacteria originating from the autochthonous microflora, like e.g. lactobacilli, to exclude pathogens from colonizing the gastrointestinal tract is a concept which has been studied rather extensively (see e.g. Alain Servin in "Antagonist activities of lactobacilli and bifidobacteria against microbial pathogens—FEMS Microbiology Reviews 2004—in press, available on line from sciencedirect website). Some of the lactic acid bacteria strains mentioned in the above literature have been highlighted for their effect in the gastrointestinal tract and been proposed as possible active agents suitable for treating various troubles or disorders caused by pathogens, e.g. diarrhoea.

The main goal of a therapy with bacterial agents should be to prevent overgrowth of pathogens until such a time that the normal vaginal or intestinal microflora can be re-established. In addition, probiotic therapy is considered as "natural" and without side effects in contrast with conventional chemical or antibiotic treatments.

Within that context it has been surprisingly observed that lactic acid bacteria strains representative of the healthy human vaginal flora which exhibited efficiency in the treatment of urogenital infections (see International Patent Application PCT/EP2004/011980 filed on Dec. 10, 2004 by Medinova A G, CH-Zurich) were also performing and consequently useful in the prophylactic or therapeutic treatment of intestinal infections or disorders initiated by gastrointestinal pathogens.

Nowadays, despite of the progresses which have already been made concerning the intimate knowledge of lactic acid bacteria (LAB) strains, their properties and their potential use in the probiotic area, there still remains a need to propose more convenient and more efficient bacteria, namely probiotic bacteria strains to the medical community.

The purpose of this invention is to provide new and useful probiotics particularly efficient in the treatment of disorders caused by various pathogens, namely infections or inflammatory diseases of the gastrointestinal tract in mammals, especially humans, respectively of the urogenital tract in females, or in the restoration of a balanced and healthy urogenital or intestinal flora after e.g. severe medical treatments like those performed with antibiotics or chemotherapeutics.

The purpose of this invention is to provide as well new methods of prophylactic or therapeutic treatment of such infections or inflammatory diseases which involve specifically selected probiotic strains.

SUMMARY OF THE INVENTION

As a first object the invention provides a method for establishing, maintaining or restoring a healthy urogenital flora and environment in females or a healthy gastrointestinal flora or environment in humans, which comprises administering thereto an effective amount of at least one probiotic strain of the genus *L. acidophilus, L. crispatus, L. gasseri, L. helveticus* and *L. jensenii* selected for their ability to kill urogenital and/or gastrointestinal pathogens and their ability to inhibit internalization of urogenital and/or gastrointestinal pathogens within gastrointestinal epithelial cells in combination with a suitable delivery system.

The invention further provides a method for establishing, maintaining or restoring a healthy urogenital flora or environment in females prior to, during and/or after pregnancy, which comprises administering thereto an effective amount of at least one of the above probiotic bacteria strains in combination with a suitable delivery system.

The invention still further provides a method for preventing or treating urogenital infections in females or gastrointestinal dysbioses and/or infections in humans which comprises administering thereto an effective amount of at least one of the above probiotic bacteria strains in combination with a suitable delivery system.

The invention still further provides a method for preventing or inhibiting the colonization and/or growth of pathogens in the urogenital tract of females or in the gastrointestinal tract of humans which comprises administering thereto an effective amount of at least one probiotic bacteria strains in combination with a suitable delivery system.

The invention still further provides a method for modulating a cellular and/or humoral immune response in humans at the vaginal and/or gastrointestinal level, or for inhibiting the inflammatory syndrome, the infectious syndrome as well as neoplasic processes in humans, which comprises administering thereto an effective amount of at least one of the above probiotic bacteria strains in combination with a suitable delivery system.

The invention also relates to probiotic compositions useful in the above methods of treatment, more specifically probiotic compositions available in the form of a food product or a beverage, e.g. those designed for clinical nutrition, a food or beverage composition, a food or beverage supplement or adjuvant designed either for human or animal consumption as Additional and more specific objects of this invention shall appear within the course of the description here below.

BRIEF DESCRIPTION OF THE DRAWINGS

FIG. 1 shows: A, Table IV—Wallace score; B, Table V—Ameho score.

DEPOSIT OF MICROORGANISM

The following microorganisms have been deposited in accordance with the terms of the Budapest Treaty with the Collection Nationale De Cultures De Microorganisms (CNCM), Paris, France, on the date indicated:

| Microorganism | Accession No. | Date of Deposit |
| --- | --- | --- |
| L. gasseri KS 120.1 | CNCM I-3218 | Jun. 4, 2004 |
| L. gasseri KS 124.3 | CNCM I-3220 | Jun. 4, 2004 |
| L. gasseri KS 114.1 | CNCM I-3482 | Jun. 4, 2004 |
| L. crispatus KS 116.1 | CNCM I-3483 | Jun. 4, 2004 |
| L. jensenii KS 119.1 | CNCM I-3217 | Jun. 4, 2004 |
| L. crispatus KS 119.4 | CNCM I-3484 | Jun. 4, 2004 |
| L. jensenii KS 121.1 | CNCM I-3219 | Jun. 4, 2004 |
| L. gasseri KS 123.1 | CNCM I-3485 | Jun. 4, 2004 |
| L. crispatus KS 127.1 | CNCM I-3486 | Jun. 4, 2004 |
| L. helveticus KS 300 | CNCM I-3260 | Jun. 4, 2004 |

The ten bacterial strains listed in the table above were deposited on Jun. 4, 2004 with the Collection Nationale De Cultures De Microorganisms (CNCM), Paris, France. These deposits were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposits. The deposits will be made available by CNCM under the terms of the Budapest Treaty, and subject to an agreement between Applicant and CNCM which assures permanent and unrestricted availability of the progeny of the culture of the deposits to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strains is not to be construed as a license to practice the invention in contravention of the rights granted under the authority of any government in accordance with its patent laws.

DETAILED DESCRIPTION OF THE INVENTION

The probiotic bacteria strains used within the frame of this invention have been first selected for their ability to adhere to epithelial cells such cervix HeLa or Caco-2 which were chosen as models. Cell adhesion is indeed a prerequisite selection feature as it conditions the capacity of the said strains to colonize epithelial tissues, e.g. that of the urogenital tract, and then to compete with, inhibit or exclude pathogens adhesion from that specific location.

These strains further exhibit a significant resistance, i.e. survival rate when exposed to the highly acidic gastric environment and a fairly good to excellent resistance when exposed to enzymes like pepsin and pancreatin as well; these properties guarantee the necessary survival of the selected strains throughout their progression within the gastrointestinal tract.

The said probiotics have been further selected for their additional ability to inhibit adhesion, growth and even survival of pathogens, namely urogenital and gastrointestinal pathogens from epithelial cells. Gram-negative or Gram-positive pathogens such as those mentioned here after are representative of those which are significantly affected by the probiotics of this invention in terms on adhesion, growth or pathogenic activity: *Salmonella* species, like *S. enterica* serovar *Typmmurium*, *E. coli*, *Streptococcus* species, e.g. *S. agalactiae*, *Staphylococcus* species like *S. aureus*, *Gardnerella* species, e.g. *G. vaginalis*, *Prevotella* species, e.g. *P. bivia*; this enumeration is of course not exhaustive.

The probiotic bacteria strains used according to the present invention have also the ability to inhibit internalization of pathogens, namely urogenital or gastrointestinal Gram-negative or Gram-positive pathogens within epithelial cells. The most efficient LAB within that frame are those which express high amounts of both hydrogen peroxide ($H_2O_2$) and lactic acid in situ where both factors act synergistically. The latter have indeed proved highly efficient against anaerobic urogenital pathogens like e.g. *Gardnerella* and *Prevotella* species.

The above probiotic bacteria strains, eventually, exhibit a further important feature, i.e. the ability to modulate the immune response of immuno-competent cells, e.g. gastrointestinal mucous membrane cells, in other words the ability to initiate, stimulate or reinforce the immune response of said cells when infected by either gram-negative or gram-positive pathogens like those mentioned here above, e.g. urogenital pathogenic *E. coli*. Due to their specific features the said LAB strains have consequently the capacity to inhibit the inflammatory syndrome of immuno-competent cells when exposed to pathogen contamination.

Quite interestingly that specific feature performs the modulation of the immune response referred to here above using two distinct routes, i.e. via the induction of either pro- or anti-inflammatory cytokines like IL 10, respectively, IL 12, TNF or IFN. It has been further observed that some LAB strains of this invention exhibit a high IFNγ induction potential, namely *L. acidophilus* KS 116.1 and *L. gasseri* KS 124.3, a feature which favors the use of same as anti-infectious agents.

That strain specificity provides consequently to the man skilled in the art the possibility to select the most appropriate strain or combination of strains for performing the medical treatment which is envisaged.

Among the LAB strains which exhibit these properties preferred species according to this invention are listed here after: *L. jensenii* KS 109, *L. gasseri* KS 114.1, *L. crispatus* KS 116.1, *L. jensenii* KS 119.1, *L. crispatus* KS 119.4, *L. gasseri* KS 120.1, *L. jensenii* KS 121.1, *L. jensenii* KS 122.1, *L. gasseri* KS 123.1, *L. gasseri* 124.3, *L. gasseri* KS 126.2, *L. crispatus* 127.1, *L. jensenii* KS 129.1, *L. jensenii* KS 130.1, *L. helveticus* KS 300 and *L. acidophilus* KS 400. Most of these strains are also representative of the healthy human vaginal micro flora.

As particularly preferred species, on can further cite the following strains:

*L. gasseri* KS 114.1 (CNCM 1-3482): gram positive—catalase negative—oxidase negative—lactic acid production 10.5 g/l—$H_2O_2$ production 10 mg/l API 50 CHI test: positive for GAL, GLU, FRU, MNE, NAG, ESC, SAL, CEL, MAL, SAC, TRE and GEN negative for: KON, GLY, ERY, DARA, LARA, RIB, DXYL, LXYL, ADO, MDX, SBE, RHA, DUL, INO, MAN, SOR, MDM, MDG, AMY, ARB, LAC5 MEL, INU, MLZ, RAF5 AMD, GLYG, XLT, TUR, LYX, TAG, DFUC5 LFUC5 DARL, LARL, GNT, 2KG and 5KG

*L. crispatus* KS 116.1 (CNCM 1-3483): gram positive—catalase negative—oxidase positive—lactic acid production 9.6 g/l—$H_2O_2$ production 2 mg/l API 50 CHI test: positive for GAL, FRU, MNE, NAG, ESC, SAL, MAL and SAC negative for: KON, GLY, ERY, DARA, LARA, RIB, DXYL, LXYL, ADO, MDX, GAL, SBE, RHA, DUL, INO, MAN, SOR, MDM, MDG, AMY, ARB, CEL, LAC, MEL, TRE, INU, MLZ, RAF, AMD, GLYG, XLT, GEN, TUR, LYX, TAG, DFUC, LFUC, DARL, LARL, GNT, 2KG and 5KG

*L. jensenii* KS 119.1 (CNCM 1-3217): gram positive—catalase negative—oxidase negative—lactic acid production 7.4 g/l—$H_2O_2$ production 20 mg/l API 50 CHI test: positive for GLU, FRU, MNE, NAG, AMY, ESC, SAL, CEL, MAL, MEL, SAC, GEN and TAG—variable for: RIB negative for: KON, GLY, ERY, DARA, LARA, DXYL, LXYL, ADO, MDX, GAL, SBE, RHA, DUL, INO, MAN, SOR, MDM, MDG, ARB, LAC, TRE, INU, MLZ, RAF, AMD, GLYG, XLT, TUR, LYX, DFUC, LFUC, DARL, LARL, GNT, 2KG and 5KG

*L. crispatus* KS 119.4 (CNCM 1-3484): gram positive—catalase negative—oxidase positive—lactic acid production 10.3 g/l—$H_2O_2$ production negative API 50 CHI test: positive for GAL, GLU, FRU, MNE, NAG, ESC, MAL, LAC, SAC and AMD negative for: KON, GLY, ERY, DARA, LARA, RIB, DXYL, LXYL, ADO, MDX, SBE, RHA, DUL, INO, MAN, SOR, MDM, MDG, AMY, ARB, SAL, CEL, MEL, TRE, INU, MLZ, RAF, GLYG, XLT, GEN, TUR, LYX, TAG, DFUC, LFUC, DARL, LARL, GNT, 2KG and 5KG

*L. gasseri* KS 120.1 (CNCM 1-3218): gram positive—catalase negative—oxidase negative—lactic acid production 10.6 g/l—$H_2O_2$ production 1 mg/l API 50 CHI test: positive for: GAL, GLU, FRU, MNE, AMY, ESC, SAL, CEL, MAL, LAC, SAC, TRE and AMD negative for: KON, GLY, ERY, DARA, LARA, RIB, DXYL, LXYL, ADO, MDX, SBE, RHA, DUL, INO, MAN, SOR, MDM, MDG, NAG, ARB, MEL, INU, MLZ, RAF, GLYG, XLT, GEN, TUR, LYX, TAG, DFUC, LFUC, DARL, LARL, GNT, 2KG and 5KG

*L. jensenii* KS 121.1 (CNCM 1-3219): gram positive—catalase negative—oxidase negative—lactic acid production 10.6 g/l—$H_2O_2$ production 1 mg/l API 50 CHI test: positive for: GAL, GLU, FRU, MNE, AMY, ARB, ESC, SAL, CEL, MAL, SAC and AMD—variable for: RIB, NAG, LAC, RAF and LFUC negative for: KON, GLY, ERY, DARA, LARA, DXYL, LXYL, ADO, MDX, SBE, RHA, DUL, INO, MAN, SOR, MDM, MDG, MEL, TRE, INU, MLZ, GLYG, XLT, GEN, TUR, LYX, TAG, DFUC, DARL, LARL, GNT, 2KG and 5KG

*L. gasseri* KS 123.1 (CNCM 1-3485): gram positive—catalase negative—oxidase negative—lactic acid production 8.5 g/l—$H_2O_2$ production 10 mg/l API 50 CHI test: positive for: GLU, MNE, NAG, ESC, MAL and SAC—variable for RJB and 5KG negative for: KON, GLY, ERY, DARA, LARA, DXYL, LXYL, ADO, MDX, GAL, FRU, SBE, RHA, DUL, INO, MAN, SOR, MDM, MDG, AMY, ARB, SAL5CEL, LAC, MEL, TRE, INU, MLZ, RAF, AMD, GLYG, XLT, GEN, TUR, LYX, TAG, DFUC, LFUC, DARL, LARL, GNT and 2KG

*L. gasseri* KS 124.3 (CNCM 1-3220): gram positive—catalase negative—oxidase negative—lactic acid production 17.0 g/l—$H_2O_2$ production 20 mg/l API 50 CHI test: positive for: GAL, GLU, FRU, MNE, NAG, ESC, SAL, MAL, SAC and TRE—variable for: RIB, AMD, GEN and 5KG negative for: KON, GLY, ERY, DARA, LARA, DXYL, LXYL, ADO, MDX, SBE, RHA, DUL, INO, MAN, SOR, MDM, MDG, AMY, ARB, CEL, LAC, MEL, INU, MLZ, RAF, GLYG, XLT, TUR, LYX, TAG, DFUC, LFUC, DARL, LARL, GNT and 2KG

*L. crispatus* KS 127.1 (CNCM 1-3486): gram positive—catalase negative—oxidase positive—lactic acid production 16.7 g/l—$H_2O_2$ production negative API 50 CHI test: positive for RIB, GAL, GLU, FRU, MNE, MAN, SOR, NAG, AMY, ESC, SAL, CEL, MAL LAC, SAC, TRE, MLZ, AMD, GLYG, GEN, TAG and GNT—variable for GLY and DXYL negative for: KON, ERY, DARA, LARA, LXYL, ADO, MDX, SBE, RHA, DUL, INO, MDM, MDG, ARB, MEL, INU, MLZ, RAF, XLT, TUR, LYX, DFUC, LFUC, DARL, LARL, 2KG and 5KG

*L. helveticus* KS 300 (CNCM 1-3360): gram positive—lactic acid production 10.45 g/kg—$H_2O_2$ production 1 mg/l API 50 CHI test—positive for: GAL, GLU, FRU, MNE, AMY, ARB, ESC, SAL, CEL, MAL, LAC, SAC, TRE and AMD negative for: RIB, MAN, GLY, SOR, KON, ERY, MLZ, DARA, LARA, LXYL, ADO, MDX, SBE, RHA, DUL, INO, MDM, MDG, MEL, INU, RAF, TAG, GNT, XLT, TUR, LYX, DFUC, LFUC, DARL, LARL, 2KG and 5KG These strains have been duly registered at the Pasteur Institute, Paris (France) in accordance with the Budapest Treaty.

According to the present invention, and due to their specific antipathogen activity, the probiotic bacteria strains mentioned here above can be used advantageously for preventing or treating urogenital infections in females and/or gastrointestinal infections in humans, more specifically humans, and for preventing or inhibiting the colonization and/or growth of pathogens in the urogenital tract or environment of females and in the gastrointestinal tract and environment of humans as well.

Also, the said probiotic bacteria strains can be used in a quite efficient way for maintaining or restoring a healthy urogenital and/or gastrointestinal flora in humans, especially humans, in particular after severe medical treatments like those performed with antibiotics.

The corresponding therapeutic or prophylactic treatments are performed by administering an effective amount of the selected strain or strains of this invention in combination with a suitable, if ever necessary food grade, delivery system, support or carrier which has been designed therefor. The terms "therapeutic treatment" used within that context mostly refer to a combined treatment where the patients have been first subject to the administration of relatively "aggressive" chemicals or antibiotics and when the convenient probiotics administration then occurs once pathogen eradication has been completed and administration of antibiotics has been stopped. The term "suitable" is meant to define a delivery system which keeps intact all the properties of the probiotic bacteria strains which are used for performing the above treatments Probiotic compositions according to this invention can further comprise usual LAB growth factors or prebiotics, e.g. dedicated natural growth factors like skim milk powder (MSK). Said compositions are preferably in the form of a food product or a beverage, a food or beverage composition like e.g. those designed for clinical nutrition, a food or beverage supplement or adjuvant designed either for human or animal consumption.

Dairy food products or beverages like fermented milks, fresh cheeses or yogurts or their dried or freeze dried equivalents represent suitable delivery systems. As e.g. food supplement or adjuvant powdered milk or milk derivatives matrixes loaded with the selected probiotics proved quite convenient. If ever necessary, said powdered matrixes can be further packaged as e.g. gelatin or cellulose capsules, gelules or tablets.

Said probiotic compositions can further comprise one or several lactic acid, i.e. probiotic or not, bacteria strains of the prior art as well and further additives like pH stabilizers, viscosity stabilizers, preservatives, antioxidants, colorants or flavors.

The compositions referred to here above may contain the selected probiotic microorganisms in amounts which can range from about $10^6$ cfu (colony forming units) to about $10^{11}$ cfu per g or dose or unit, preferably in a form that keeps their viability and their specificity intact, e.g. in a encapsulated or lyophilized form. The ultimate details of said compositions as well as their dosage shall depend, eventually, on the specific application they are intend for, the age or health status of the patients or person the be treated, the nature of the pathogen contamination or the benefit expected from preventive administration of the probiotics. It is within current skills and expertise of the medical or nutritional community to adjust all the relevant parameters.

When compared to prior known reference strains (see examples below) the probiotic bacteria strains selected within the frame of the present invention have shown either a similar or even higher antipathogen activity depending on the experimental model which has been selected therefor.

The following examples illustrate only some of the embodiments of this invention and so are not intended to constitute any limitation or restriction thereof.

EXAMPLES

Material and Methods

| Tested Srain | Code |
|---|---|
| hensenii 109 | KS 109 |
| crispatus 116.1 | KS 116.1 |
| jensenii 119.1 | KS 119.1 |
| gasseri 120.1 | KS 120.1 |
| jensenii 121.1, | KS 121.1 |

-continued

| Tested Srain | Code |
|---|---|
| jensenii 122.1 | KS 122.1 |
| gasseri 123.3 | KS 124.3 |
| gasseri 126.2 | KS 126.2 |
| jensenii 129.1 | KS 129.1 |
| L. jensenii 130.1 | KS 130.1 |
| helveticus 300 | KS 300 |
| acidophilus 400 | KS 400 |

The control adhering lactobacilli strain are the L. casei rhamnosus strain GG (ATCC Accession no 53103), the L. rhamnosus strain GR-I (ATCC Accession no 55826) and the L. fermentum strain RC-14 (ATCC Accession no 55845).

All the lactobacilli strains were grown in De Man, Rogosa, Sharpe (MRS) broth (Biokar Diagnostic, Beauvais, France) for 18 h at 37° C.

Bacterial Pathogens.

Salmonella enterica serovar Typhimurium strain SL 1344 was a gift of B.A.D. Stacker (Stanford, Calif.). Bacteria were grown overnight for 18 h at 37° C. in Luria broth (Difco Laboratories).

Uropathogenic diffusely-adhering Escherichia coli strains IH1 1128 and 7372, and diarrheagenic strain C 1845 were gifts from B. Nowicki (Texas University, Galvestone) and S. Moseley (Seattle University). Strain 7372 carriers the class II papG allele, the hly gene (haemolysin) and the Dr operon. Strain IH1 1128 carriers the Dr operon. Strain C1845 carriers the Daa operon. All bacterial strains were maintained on LB plates and prior to infection, bacteria were grown in LB broth at 37° C. for 18 h.

Staphylococcus aureus strain was from the Pasteur culture collection (Paris). Bacteria were grown overnight at 370 C in TSA broth (Difco Laboratories).

Strains of Streptococcus agalactiae DSM 2134, Gardnerella vaginalis DSM 4944, Prevotella bivia Cl-I (DSM 20514) and Candida albicans DSM 1386 were from Medinova Ltd, Zurich, Switzerland). Staphylococcus aureus strain was from the Pasteur culture collection (Paris). Bacteria were grown overnight at 37° C. in TSA broth (Difco Laboratories). Streptococcus agalactiae strain was grown overnight at 370 C in BHI broth (Difco Laboratories).

Candida albicans strain was grown overnight at 37° C. in Sabouraud broth. Gardnerella vaginalis was grown on Gardnerella agar plates purchased from BioMerieux France.

Bacteria were suspended in buffered sodium chloride-peptone solution pH 7.0 to about $10^6$ colony forming unit (CFU/ml). 500 µl or the prepared suspensions were spread out on the agar plate. The inoculated plates were dried under sterile laminar air flow conditions. The agar plates were then incubated under anaerobic conditions using a sealed anaerobic jar (Becton Dickinson, USA) at 370 C for 36° h in maximum. Before use, the Gardnerella vaginalis strain was sub-cultured in BHI supplemented with yeast extract, maltose and horse serum, under anaerobic conditions using a sealed anaerobic jar at 37° C. for 36 h in maximum.

Before use, bacterial cultures were centrifuged at 5.500×g for 5 min at 4° C. The culture medium was discarded and the bacteria were washed once with phosphate-buffered saline (PBS) and re suspended in PBS.

Cell Lines and Cultures.

Human cervical HeLa cells were cultured at 37° C. in a 5% $CO_2$-95% air atmosphere in RPMI 1640 with L-glutamine (Life Technologies) supplemented with 10% heat-inactivated (30 min, 56° C.) foetal calf serum (FCS; Boehringer, Mannheim, Germany). Cells were used for infection assays before confluence, i.e., after 5 days in culture.

The human intestinal cell line used was the TC7 clone (Caco-2/TC7), established from the parental Caco-2 cell line. Cells were routinely grown in Dulbecco modified Eagle's minimal essential medium (DMEM) (25 mM glucose) (Invitrogen, Cergy, France), supplemented with 15% heat-inactivated (30 min, 56° C.) foetal calf serum (Invitrogene) and 1% non-essential amino acids (Invitrogene) as previously described. For maintenance purposes, cells were passaged weekly using 0.02% trypsin in $Ca^{2+}Mg^{2+}$-free PBS containing 3 mM EDTA. Experiments and maintenance of the cells were carried out at 37° C. in a 10% $CO_2$/90% air atmosphere. The culture medium was changed daily. Cells were used at post-confluence after 15 days of culture (fully differentiated cells) for infection assay of *S. enterica* serovar *Typhimurium*.

Adhesion Assays.

The adhesion of lactobacilli strains onto cervix HeLa cells and intestinal Caco-2/TC7 cells was examined according to the following steps: the cells monolayers were washed twice with phosphate-buffered saline (PBS). For each adhesion assay, 0.5 ml of the *Lactobacillus* suspension (bacteria with spent broth culture supernatant) was mixed with DMEM (0.5 ml), and then added to each well of the tissue culture plate (24 wells) which was then incubated at 37° C. in 10% $CO_2$/90% air. The final concentrations of bacteria examined were $1\times10^8$, $2\times10^8$, $1\times10^9$, and $2\times10^9$ bacteria per ml. After 1 h incubation, the monolayers were washed five times with sterile PBS, fixed with methanol, stained with Gram stain, and then examined microscopically under oil immersion. Each adhesion assay was conducted in duplicate with cells from three successive passages. For each assay, the number of adherent bacteria was determined in 20 random microscopic areas (adhesion score: 0 to 5). Moreover, the level of viable adhering lactobacilli was determined by quantitative determination of bacteria associated with the infected cell monolayers. After being infected, cells were washed twice with sterile PBS and lysed with sterilized $H_2O$. Appropriate dilutions were plated on tryptic soy agar (TSA) to determine the number of viable cell-associated bacteria by bacterial colony counts.

Each cell-association assay was conducted at least in triplicate, with three successive cell passages. Results were expressed as CFU/ml of cell-associated bacteria.

Activity Against the Growth of Pathogens.

A culture medium containing MRS (5 ml) and specific pathogen culture medium (5 ml) was inoculated with 0.1 ml of a cultivated pathogen and 0.1 ml of cultured *Lactobacillus* strain. Control was a culture medium inoculated with 0.1 ml of a cultivated pathogen and 0.1 ml of non-cultivated MRS adjusted to pH 4.5. At indicated time-points, aliquots were removed, serially diluted and plated on tryptic soy agar to determine bacterial colony counts of pathogen. Each assay was conducted at least in triplicate. Results were expressed as CFU/ml.

Activity Against the Viability of Pathogens.

Colony count assays were performed by incubating $10^8$ CFU/ml pathogen (0.5 ml) with the lactobacilli culture ($10^8$ CFU/ml, 0.5 ml) at 37° C. Control was non-cultivated MRS adjusted to pH 4.5. Initially and at predetermined intervals, aliquots were removed, serially diluted and plated on tryptic soy agar to determine bacterial colony counts of pathogen. Each assay was conducted at least in triplicate. Results were expressed as CFU/ml.

Inhibition of Uropathogenic *E. coli* Adhesion onto Epithelial HeLa Cells.

For cell monolayer infection, pathogens were cultured at 37° C. for 18 h in appropriate culture media as described above. Prior to infection, the cell monolayers, prepared in twenty four-well TPP tissue culture plates (ATGC, Paris, France), were washed twice with PBS. Infecting bacteria were suspended in the culture medium and a total of 0.5 ml DMEM+0.25 ml culture pathogen ($1\times10^8$ CFU/ml)+0.25 ml lactobacilli culture ($1.5\times10^9$ CFU/ml) were added to each well of the tissue culture plate. The plates were incubated at 37° C. in 10% $CO_2$/90% air for different time of infection as indicated and then were washed three times with sterile PBS and lysed with sterilised $H_2O$. Appropriate dilutions were plated on tryptic soy agar to determine the number of viable cell-associated bacteria by bacterial colony counts. Each assay was conducted in triplicate with three successive passages of HeLa cells.

Analysis.

Results are expressed as means±standard error to the mean. For statistical comparisons, Student's t test was performed.

Results

Example 1

1. Adhesion Capacity of *L. Jensenii* KS 119.1 and KS 130.1, *L. Crispatus* KS 116.1 and *L. Gasseri* KS 124.3 onto HeLa and Caco-2/TC7 Cells.

The level of adhesion of the above strains was determined after the cells were inoculated with four concentrations of lactobacilli ($5\times10^7$; $1\times10^8$; $5\times10^8$; $1\times10^9$ CFU/well). Generally, a concentration-dependent adhesion was observed.

In cervix HeLa cells, adhesion levels observed show that all the tested strains are adhering. The *L. jensenii* KS 119.1 and KS 130.1 strains appeared the best adhering strains (7.5 log CFU/ml at $5\times10^8$ CFU/well) as compared with the control adhering strains, *L. casei rhamnosus* GG and *L. rhamnosus* GR1 strains.

In intestinal Caco-2/TC7 cells, adhesion levels observed show that all the Medinova strains are adhering. The *L. crispatus* KS 116A, *L. jensenii* 119.1, 129.1 and KS 130.1, *L. gasseri* 124.3 strains appeared the best adhering strains (7.5-8 logs CFU/ml at $5\times10^8$ CFU/well) as compared with the control adhering strains, *L. casei rhamnosus* GG and *L. rhamnosus* GR1 strains.

As observed by scanning electron microscopy, all the "invention lactobacilli strains" appeared adhering in close contact with the HeLa and Caco-2/TC7 cells.

On the basis of their adhering properties, the *L. crispatus* KS 116.1 and *L. jensenii* 119.1 have been selected for the following studies of antibacterial activities against urogenital and intestinal pathogens.

2. Activity of KS 116.1 and KS 119.1 on the Growth of Urogenital and Intestinal Pathogens.

It has been examined whether the above mentioned strains are active on the growth of *Staphylococcus aureus, Streptococcus agalactiae*, uropathogenic and diarrheagenic *E. coli*, and diarrheagenic *Salmonella enterica* serovar *Typhimurium*. The growth of pathogens was measured at 5, 8, 18 and 24 h.

For *Staphylococcus aureus*, the control *L. rhamnosus* strain GR-I and *L. fermentum* strain RC-14 inhibited the growth of bacteria. Similarly, *L. crispatus* KS 116.1 and *L. jensenii* 119.1 inhibited the growth of *Staphylococcus aureus* and showed a decrease in the viable bacteria number. When activities of lactobacilli strains were compared, the *L. jensenii* 119.1 appeared the most active strain.

For uropathogenic *E. coli* strains IH1 1128 and 7372, the control *L. rhamnosus* strain GR-1 and *L. fermentum* strain RC-14 inhibited the growth of the bacteria. Similarly, *L. crispatus* KS 116.1 and *L. jensenii* KS 119.1 inhibited the growth of *E. coli*. When activities of lactobacilli strains were compared, the *L. jensenii* 119.1 appeared the most active strain.

For diarrheagenic *E. coli* strain C1845, the control *L. rhamnosus* strain GR-I and *L. fermentum* strain RC-14 inhibited the growth of the bacteria. Similarly, *L. crispatus* KS 116.1 and *L. jensenii* KS 119.1 inhibited the growth of *E. coli*. When activities of lactobacilli strains were compared, the same activity was found for all the lactobacilli strains examined.

For diarrheagenic *S. enterica* serovar *Typhimurium* strain SL1 344, the control *L. rhamnosus* strain GR-I and *L. fermentum* strain RC-14 inhibited the growth of the bacteria. Similarly, *L. jensenii* 119.1 inhibited the growth of *S. enterica* serovar *Typhimurium*. When activities of lactobacilli strains were compared, the same activity was found for the control *L. rhamnosus* strain GR-I and *L. fermentum* strain RC-14 and *L. jensenii* KS 119.1. In contrast, the *L. crispatus* KS 116.1 showed a lower activity.

For *Candida albicans* no activity was found for the control *L. rhamnosus* strain GR-I and *L. fermentum* strain RC-14, and *L. crispatus* KS 116.1 and *L. jensenii* KS 119.1.

3. Killing Activity of KS 116.1 and KS 119.1 Against Urogenital and Intestinal Pathogens.

It has been examined whether said lactobacilli are active on the viability of *Staphylococcus aureus, Streptococcus agalactiae*, uropathogenic and diarrheagenic *E. coli*, and diarrheagenic *Salmonella enterica* serovar *Typhimurium*. The effect on viability of pathogens was measured at 2, 3, and 4 h.

For *Staphylococcus aureus*, the control *L. rhamnosus* strain GR-I and *L. fermentum* strain RC-14, and *L. jensenii* 119.1 decreased for 2 logs the viability of bacteria. In contrast, the *L. crispatus* KS 116.1 showed no activity.

For *Streptococcus agalactiae*, the control *L. rhamnosus* strain GR-I and *L. fermentum* strain RC-14, and *L. jensenii* 119.1 and *L. crispatus* KS 116.1 showed no activity.

For uropathogenic *E. coli* strains IH11128 and 7372, the control *L. rhamnosus* strain GR-1 and *L. fermentum* strain RC-14 showed 4 logs of decrease in viability of bacteria. *L. crispatus* KS 116.1 and *L. jensenii* 119.1 were not active showing only one log of decrease in viability of the bacteria.

For diarrheagenic *E. coli* strain C1845, both of the control *L. rhamnosus* strain GR-I and *L. fermentum* strain RC-14, and *L. crispatus* KS 116.1 and *L. jensenii* 119.1 showed a low activity on the viability of C1845 bacteria (2 logs of decrease).

For diarrheagenic *S. enterica* serovar *Typhimurium* strain SL1344, both of the control *L. rhamnosus* strain GR-I and *L. fermentum* strain RC-14, and *L. crispatus* KS 116.1 and *L. jensenii* 119.1 showed a great activity by decreasing the viability of SL1344 bacteria (5 logs of decrease).

For *Gardnerella vaginalis*, the control *L. rhamnosus* strain GR-I and and *L. fermentum* strain RC-14, and *L. fermentum* strain RC-14, and *L. jensenii* 119.1 decreased for 2 logs the viability of *Gardnerella*. In contrast, the *L. crispatus* KS 116.1 showed no activity.

For *Candida albicans* no activity was found for the control *L. rhamnosus* strain GR-I and *L. fermentum* strain RC-14, and *L. crispatus* KS 116.1 and *L. jensenii* KS 119.1.

4. Inhibition of the Adhesion of Uropathogenic *E. Coli* Strain IH1 1128 Strain onto HeLa Cells by KS 116.1 and KS 119.1.

It has been examined whether said lactobacilli are able to inhibit the adhesion of uropathogenic *E. coli* strain IH11128 onto HeLa cells. The effect of the control *L. rhamnosus* strain GR-I and *L. fermentum* strain RC-14, and *L. jensenii* 119.1 and *L. crispatus* KS 116.1 was measured at three concentrations: $1 \times 10^8$, $5 \times 10^8$, and $1 \times 10^9$ bacteria per well.

A 30 to 40% of inhibition of IH11128 adhesion was found at a concentration of $1 \times 10^8$ bacteria per well for the control *L. rhamnosus* strain GR-I and *L. fermentum* strain RC-14. At this concentration, the *L. jensenii* KS 119.1 and *L. crispatus* KS 116.1 were inactive. Inhibition of IH11128 adhesion was effective at a concentration of $5 \times 10^8$ bacteria per well for *L. jensenii* 119.1 and *L. crispatus* KS 116.1 and a similar inhibition that those obtained with the control *L. rhamnosus* strain GR-I and *L. fermentum* strain RC-14 was observed. A similar high inhibition level of IH11128 adhesion was observed with the control *L. rhamnosus* strain GR-I and *L. fermentum* strain RC-14, and *L. jensenii* KS 119.1 and *L. crispatus* KS 116.1 at the concentration of $1 \times 10^9$ bacteria per well.

Example 2

1. Activity of *L. Gasseri* KS 124.3, *L. Helveticus* KS 300 and *L. Acidophilus* KS 400 on the Growth of Urogenital and Intestinal Pathogens.

It has been examined whether the strains referred to here above are active against the growth of *Staphylococcus aureus, Streptococcus agalactiae, Candida albicans* and uropathogenic and diarrheagenic *E. coli* strains IH11128 and 7372. The growth of pathogens was measured at 5, 8, 18 and 24 h.

No activity was developed against *Streptococcus agalactiae* and *Candida albicans* by *L. gasseri* KS 124.3, *L. helveticus* KS 300 and *L. acidophilus* KS 400 as well as by the control strains GR-I and RC-14.

Concerning *Staphylococcus aureus*, the control *L. rhamnosus* strain GR-I and *L. fermentum* strain RC-14 efficiently inhibited the growth of the bacteria. Similarly, *L. gasseri* KS 124.3, *L. helveticus* KS 300 and *L. acidophilus* KS 400 inhibited the growth of *Staphylococcus aureus* and showed a decrease in the viable bacteria number. When activities of lactobacilli strains were compared, the *L. helveticus* KS 300 appeared the most active strain.

For uropathogenic *E. coli* strains IH11128, the control strains *L. rhamnosus* GR-I and *L. fermentum* RC-14 efficiently inhibited the growth of the bacteria. Similarly, *L. helveticus* KS 300 efficiently inhibited the growth of *E. coli*. When activities of lactobacilli strains were compared, a lower activity appeared for *L. gasseri* KS 124.3 and *L. acidophilus* KS 400.

For uropathogenic *E. coli* strain 7372, both control strains *L. rhamnosus* GR-I and *L. fermentum* RC-14 strains inhibited the growth of bacteria. Similarly *L. helveticus* KS 300 inhibited the growth of said bacteria whereas *L. acidophilus* KS 400, however, was active only at 25 hours.

2. Killing Activity of KS 124.3, KS 300 and KS 400 Against Urogenital and Intestinal Pathogens.

It has been examined whether said lactobacilli are active on the viability of *Staphylococcus aureus, Streptococcus agalactiae, Candida albicans*, uropathogenic *E. coli* IH1 1128 and 7372, diarrheagenic *E. coli* Cl 845 and *Gardnerella vaginalis*. The effect on viability of pathogens was measured at 2, 3, and 4 h.

For *Staphylococcus aureus*, the control strains *L. rhamnosus* GR-I and *L. fermentum* RC-14, and *L. gasseri* KS 124.3, *L. helveticus* KS 300 and *L. acidophilus* KS 400 decreased for 2-3 logs the viability of bacteria.

Concerning *Streptococcus agalactiae* and *Candida albicans* the two control strains and *L. gasseri* KS 124.3, *L. helveticus* KS 300 and *L. acidophilus* KS 400 showed no activity.

For uropathogenic *E. coli* strains IH11128, the control strains *L. rhamnosus* strain GR-I and *L. fermentum* RC-14 and *L. helveticus* KS 300 as well showed 3 logs of decrease in viability of the bacteria. *L. acidophilus* KS 400 and *L. gasseri* KS 124.3 were not active.

Concerning uropathogenic *E. coli* strains 7372, the control strains showed 2 logs of decrease in viability of the bacteria. *L. helveticus* KS 300 showed 3 logs of decrease whereas *L. acidophilus* KS 400 and *L. gasseri* KS 124.3 were not active within the same conditions.

For *Gardnerella vaginalis*, both control strains, *L. acidophilus* KS 400 and *L. gasseri* KS 124.3 showed 3 logs of decrease in viability of the bacteria. A rapid and efficient activity was observed for *L. helveticus* KS 300, higher than that found for the above control strains.

For diarrheagenic *E. coli* strain C1845, both of the control strains *L. rhamnosus* GR-I and *L. fermentum* RC-14 killed the bacteria showing a 3 log decrease in the viability of same. Similar effect was observed for *L. gasseri* KS 124.3 whereas no activity was detected concerning *L. acidophilus* KS 400. *L. helveticus* KS 300 exhibits a killing which is definitely higher that that observed for the above control strains.

Example 3

1. Killing Activity of *L. Jensenii* KS 121.1 and KS 122.1, *L. Gasseri* KS 120.1 and *L. Helveticus* KS 300 Against Urogenital and Intestinal Pathogens.

It has been examined whether said *lactobacillus* strains are active on the viability of *Streptococcus agalactiae, Candida albicans*, uropathogenic *E. coli* IH11128, *Gardnerella vaginalis, Prevotella bivia* and *Salmonella enterica Typhimurium*. The effect on viability of pathogens was measured at 4 h of contact.

Concerning both *Streptococcus agalactiae* and *Candida albicans* none of the tested lactobacilli showed an activity.

For uropathogenic *E. coli* strains IH11128, *L. jensenii* KS 121.1 and KS 122.1 showed no activity whereas, in contrast, *L. gasseri* KS 120.1 decreased efficiently (4 logs) the viability of *E. coli* in unshaken conditions. *L. helveticus* KS 300 and the *L. fermentum* RC-I control strain decreased of 2 logs the viability of *E. coli* in unshaken conditions only.

Concerning *Gardnerella vaginalis*, both *L. jensenii* KS 121.1 and KS 122.1 showed no activity. In contrast *L. gasseri* KS 120.1 decreased efficiently (6 logs) the viability of *Gardnerella vaginalis* in unshaken conditions; *L. helveticus* KS 300 showed similar efficiency (4 logs of decrease) in unshaken conditions also, whereas control strain showed a 3 log of decrease only.

For *Prevotella bivia, L. gasseri* KS 120.1, *L. jensenii* 122.1, *L. helveticus* KS 300 and the control strain *L. fermentum* RC-14 decreased viability of the bacteria for 2 logs, in unshaken conditions. *L. jensenii* KS 121.1 which was highly active against *Prevotella bivia* in unshaken conditions had lost its activity when tested in shaken conditions.

Concerning *Salmonella Typhimurium, L. gasseri* KS 120.1 (3 logs), *L. jensenii* KS 121.1 and KS 122.1, *L. helveticus* KS 300 and the control strain *L. fermentum* RC-14 were quite active (6 logs of decrease) in unshaken conditions. *L. gasseri* KS 120.1 remained active even in shaken conditions.

2. Activity of KS 120, KS 121.1, KS 122.1 and KS 300 on the Growth of *Gardnerella Vaginalis* and *Prevotella Bivia*

The tests have been performed in both shaken and unshaken conditions.

In unshaken conditions *L. jensenii* KS 121.1 and KS 122.1 inhibited the growth of *Gardnerella vaginalis* whereas *L. gasseri* 120.1, *L. helveticus* and the control strain *L. fermentum* RC-14 inhibited said activity at still a higher level.

In shaken conditions *L. jensenii* KS 121.1 and KS 122.1 and *L. helveticus* as well have lost their activity, whereas *L. gasseri* 120.1 remains active (2 logs of decrease) against *Gardneralla vaginalis*.

In both shaken and unshaken conditions *L. gasseri* KS 120.1, *L. jensenii* KS 121.1 and KS 122.1, *L. helveticus* KS 300 and the control strain inhibited the growth of *Prevotella bivia* at a high level.

3. Inhibition of Adhesion of *Gardnerella Vaginalis* and *Prevotella Bivia* onto HeLa Cells KS 120.1, KS 121.1 and KS 300

The effect of *L. gasseri* KS 120.1, *L. helveticus* KS 300 of the control strains *L. fermentum* RC-14 as well as *L. casei rhamnosus* GG was measured at the concentration of $1 \times 10^9$ bacteria per well.

The control *L. fermentum* RC-14 strain and *L. jensenii* KS 121.1 decreased for 2 logs the level of adhesion of *Gardnerella vaginalis* on the tested cells. *L. gasseri* KS 120.1 and *L. helveticus* KS 300 decreased said adhesion for 4 logs.

*L. jensenii* KS 121.1 decreased adhesion of *Prevotella bivia* for 1 log only, whereas *L. gasseri* KS 120.1, *L. helveticus* KS 300 as well as the control strain RC-14 decreased said adhesion for 2 logs.

4. Inhibition of Adhesion and Internalization of Uropathogenic *E. Coli* Strain IH1 1128 Strain onto HeLa Cells by KS 120.1, KS 121.1 and KS 300

A strategy often used by extra-intestinal pathogens like *E. coli* to evade host defence mechanism is to establish a local reservoir within epithelial cells (M. A. Muvlea in *Eschrichia coli*. Cell Microbiol. 4, 257-271—2002) and cell entry by IH11128 strain appears to be an effective mechanism for promoting prolonged persistence these pathogens in the urinary tract.

The effect of *L. gasseri* KS 120.1, *L. helveticus* KS 300 and of the control strains RC-14 and GG strain was examined concerning the above uropathogenic *E. coli.: L. jensenii* 121.1 decreased for 2 logs the level of viable internalized *E. coli*, whereas *L. gasseri* 120.1, *L. helveticus* and both the control strains have shown a 4 logs of decrease of the internalized *E. coli*.

Example 4

Determination of the Resistance to Pepsin (% Survival at To+X Min)

4.1 The LAB strains selected for that experiment have been grown in 10 ml of MRS broth at 37° C. during 24 hours after which the cell culture was centrifuged for 5 min at 4000 rpm. The pellet thus obtained was then washed 3 times in a PBS buffer (pH 7) and subsequently suspended in 1 ml of said PBS buffer.

4.2 200 µl of the above cell suspension was added to a series of 4 test tubes containing each 1 ml of a filtered pepsin solution at pH 2 and 300 µl of aqueous NaCl. Immediately after inoculation ($T_0$) a 10-fold dilution series of 100 µl cell suspension from tube no 1 was made using a Ringer solution and subsequently plated on MR agar for incubation at 37° C. during 24 hours. The same procedure was also performed concerning each of the remaining tubes, at T+20, T+40 and T+60 min respectively. Corresponding bacteria (CFU) counts are reported in Table I here below:

TABLE I

| Strain | 5 min | 20 min | 40 min | 60 min |
|---|---|---|---|---|
| KS 116.1 | 81 | 70 | 0 | 0 |
| KS 400 | 76 | 42 | 5 | 0 |
| KS 119.1 | 67 | 0 | 0 | 0 |
| KS 121.1 | 97 | 232 | 187 | 222 |
| KS 120.1 | 79 | 128 | 161 | 189 |
| KS 124.3 | 100 | 16 | 2 | 0 |
| KS 300 | 75 | 75 | 45 | 4 |

One observes that *L. jensenii* KS 121.1 and *L. crispatus* KS 120.1 strains are particularly resistant to pepsin, even after a prolonged period.

Example 5

Determination of the Resistance to Pancreatin (% Survival at T0+X Min)

5.1 The LAB strains selected for that experiment have been grown in 10 ml of MRS broth at 37° C. during 24 hours after which the cell culture was centrifuged for 5 min at 4000 rpm. The pellet thus obtained was then washed 3 times in a PBS buffer (pH 7) and subsequently suspended in 1 ml of said PBS buffer 5.2 200 µl of the above cell suspension was added to a series of 5 test tubes containing each 1 ml of a 0.1% porcine pancreatin solution at pH 8 and 300 µl of aqueous NaCl. Immediately after inoculation ($T_0$) a 10-fold dilution series of 100 µl cell suspension from tube no 1 was made using a Ringer solution and subsequently plated on MR agar for incubation at 37° C. during 24 hours. The same procedure was also performed concerning each of the remaining tubes, at T+20, T+40, T+60 and T+120 min respectively. Corresponding bacteria (CFU) counts are reported in Table II here below:

TABLE II

| Strain | 5 min | 20 min | 40 min | 60 min | 120 min |
|---|---|---|---|---|---|
| KS 116.1 | 152 | 135 | 185 | 181 | 175 |
| KS 400 | 107 | 160 | 127 | 93 | 206 |
| KS 119.1 | 78 | 113 | 140 | 160 | 151 |
| KS 121.1 | 65 | 48 | 63 | 110 | 55 |
| KS 120.1 | 181 | 167 | 119 | 129 | 116 |
| KS 124.3 | 50 | 88 | 119 | 129 | 116 |
| KS 300 | 71 | 80 | 86 | 93 | 71 |

One observes that *L. acidophilus* KS 116.1 and KS 400, as well as *L. jensenii* KS 119.1, *L. crispatus* 120.1 and KS 124.3 strains, but to a lesser extent, are particularly resistant to pancreatin. Quite interestingly *L. crispatus* KS 120.1 is resistant to both pepsin and pancreatin.

Example 6

Modulation of the Immune Response (In Vivo Test Using Human PMBC)

The following strains have been tested within the conditions set hereafter concerning their ability to induce or modulate or affect an immune response, more specifically their ability to induce the secretion of cytokines and the like: *L. crispatus* KS 116.1, *L. jensenii* 119.1, *L. jensenii* KS 121.1 and KS 122.1, *L. gasseri* KS 120.1, *L. gasseri* KS 124.3, *L. helveticus* KS 300 and *L. acidophilus* KS 400.

The detection of the induction of cytokines was made by means of a test for in vitro stimulation of isolated peripheral blood mononuclear cells (PBMC). Among the cytokines induced during these tests, there are interleukins 10 and 12 (IL10 & IL 12), γ-interferon (γ-IFN) and tumor necrosis factor α (TNFα).

Experimental Procedures

PMBC preparation: Fresh human blood obtained for healthy subjects (four donors) was diluted at a 1:2 ratio with PBS-Ca (GIBCO) and purified on a Ficoll gradient (GIBCO). After centrifugation at 400×g for 30 min at 20° C. the peripheral blood monocular cellular cells (PMBC's) formed an interphase ring layer in the serum. PMBC's were aspired carefully, suspended to a final volume of 50 ml using PBD-Ca and washed three times in the same buffer with centrifugation steps at 350×g for 10 min at 20° C.

PMBC's were subsequently resuspended using complete RPMI medium (GIBCOP),m supplemented with 10% w/v L-glutamine (GIBCO) and gentamycin (150 µg/ml) (GIBCO). PBMC's were counted under the microscope and adjusted at a concentration of $2\times10^6$ cells/ml and distributed (in 1 ml aliquots) in 24-well tissues culture plates (Corning, Inc.).

Bacteria preparation: overnight LAB cultures were washed twice with PBS buffer, pH 7.2 before being resuspended in PBS at concentration of $2\times10^9$ cfu/ml.

PMBC incubation: from these suspensions 10 µl was transferred into wells of the PMBC plates which were incubated at 37° C. in a 5% $CO_2$/95% air atmosphere. After 24 hours incubation the supernatant was aspirated, centrifuged at 2000 rpm and the supernatant removed and stored at −20° C. The control consisted of bacteria-free buffer.

Cytokine quantification: cytokine expression levels have been determined by ELISA tests («Enzyme linked immuno sorbent assay»). ELISA plates are coated with anti-cytokine antibody (overnight procedure) and the antibody is blocked with PBS/BSA 1%. A proper standard was prepared with known concentrations of cytokines, covering the detection range of 15.62 to 2000 pg/ml (incubated overnight).

The anti-cytokine detection and quantification was performed with the streptavidine reaction on substrate (TMB Pharmigen). The commercial kits Pharmigen have been used according to the manufacturer's description. Four cytokines were determined: the pro-inflammatory/Th 1 cytokines TNFα, IFNγ, IL 12 and the anti-inflammatory/Th 2 cytokine IL10.

TABLE III

| | IL10 | IL 12 | TNFα | IFNγ | IL10/IL12 |
|---|---|---|---|---|---|
| Control | 31.25 | 31.25 | 31.25 | 31.25 | 1 |
| KS 120.1 | 1228.67 | 176.32 | 17698.83 | 3513.36 | 6.96840971 |
| KS 121.1 | 2297.87 | 47.66 | 14180.66 | 897.65 | 48.2138061 |
| KS 116.1 | 2856.26 | 167.6 | 33569.91 | 7209.33 | 17.0540573 |
| KS400 | 3177.49 | 103.85 | 26799 | 6949.13 | 30.5969186 |
| KS 300 | 2290.47 | 59.7 | 18703.66 | 10047.75 | 38.3663317 |
| KS 119.1 | 307.13 | 198.47 | 6693.3 | 9192.74 | 1.54748829 |
| KS 124.3 | 2969.02 | 660.98 | 31307.71 | 16985.56 | 4.49184544 |

Observations
- a high level of TNFα induction for all the tested LAB strains
- a relatively low level of INFγ concerning *L. jensenii* KS 121.1
- the highest IL10 induction potential concerning *L. crispatus* KS 116.1 and KS 400
- in contrast to the two *L. jensenii* strains the two *L. gasseri* strains have shown a similar profile, especially when considering the ratio's in IL10/IL12 and in TNFα/INFγ.

Within the above testing frame it is clear that the cytokine induction profile is strain specific.

Example 7

Determination of the Anti-Inflammatory Activity (In Vivo Test Using an Animal Model)

An acute model of mice has been adapted from Camoglio et al. (see Eur. J. Immunol. 2000) where the animals have been fed from day −5 to day +2 with selected lactic acid bacteria strains, at a rate of $10^8$ bacteria per mouse per day. TNBS was then injected on day zero, at a rate of 120 mg/kg mice in order to induce acute colitis and the animals have been sacrificed at day +2 and eventually subjected to both macroscopic (Wallace score—Table IV) and histological (Ameho score—Table V) scoring (FIG. 1).

These tables clearly show that the selected lactic acid bacteria strains exhibit a significant anti-inflammatory effect when compared to reference strains.

Example 8

Probiotic Composition for Local Administration 8.1 Vaginal Capsules

Samples of the LAB strains of this invention (see above) have been cultured for min. 24 hours in conditions similar to those mentioned here above. The cultured strains have been isolated, washed and lyophilized individually, individually suspended in a lactose/MSK powder mixture and eventually divided into unit doses each of them containing about $10^8$-$10^9$ cfu (colony forming units).

Said unit doses have been then poured into gelatin vaginal capsules each of them comprising about $10^8$-$10^9$ cfu of selected LAB strains of this invention.

8.2 Vaginal Suppositories

Soft vaginal suppositories have been prepared using the following ingredients:
- buffered lactic acid solution—lactose
- PEG 4000
- PEG 600

The adequate amount of selected lyophilized LAB strains of this invention has been then added to unit doses to afford vaginal suppositories each comprising about $10^8$-$10^9$ cfu.

Example 9

Composition for Oral Administration 9.1 Food Supplement

Edible cellulose capsules (hydroxypropyl methyl cellulose) each comprising about $10^8$-$10^9$ cfu of selected LAB strains of this invention have been manufactured using filler comprising the following ingredients:

- dehydrated yogurt powder
- anhydrous dextrose potato starch
- microcrystalline cellulose
- selected lyophilized LAB strain.

9.2 Fermented Milk Product (Yogurt)

Portions of a so called "Yogurt Nature Light" have been prepared using the following process: to a batch of standardized 1.5% fat milk there was added 3% of skimmed milk powder (MSK) and the whole was then pasteurized at 90° C. for 30 minutes. 1% volume of commercial starter cultures of *L. bulgaricus* and *S. thermophilus* have been added to the pasteurized milk; then the whole was gently stirred at room temperature, disposed in 100 ml containers which were all eventually incubated at 40° C. during around 4 hours to afford the desired pH.

Then portions of selected lyophilized LAB strains of this invention were added to the yogurt cans in such an amount to have about $10^8$-$10^9$ cfu per ml yogurt can and a further incubation was carried out for about 30 min. until to afford a pH of about 4.5 to 4.7. These yogurt portions can be stored at 4° C. before consumption.

What is claimed is:

1. A method of establishing, maintaining or restoring a healthy urogenital flora and environment in a female or a healthy gastrointestinal flora or environment in a human comprising administering to said female or said human a probiotic composition comprising an effective amount of at least one probiotic strain of the genus *L. crispatus, L. gasseri, L. helveticus* and *L. jensenii* selected from the group consisting of *L. crispatus* KS 116.1 (CNCM I-3483), *L. crispatus* KS 119.4 (CNCM I-3484), *L. crispatus* 127.1 (CNCM I-3486), *L. gasseri* KS 114.1 (CNCM I-3482), *L. gasseri* KS 120.1 (CNCM I-3218), *L. gasseri* KS 123.1 (CNCM I-3485), *L. gasseri* KS 124.3 (CNCM I-3220), *L. helveticus* KS 300 (CNCM I-3360), *L. jensenii* KS 119.1 (CNCM I-3217) and *L. jensenii* KS 121.1 (CNCM I-3219).

2. The method of claim 1, wherein the probiotic composition comprises a mixture of *Lactobacillus* strains, the mixture comprising *L. gasseri* KS 120.1 (CNCM I-3218) in combination with at least one of *L. jensenii* KS 119.1 (CNCM I-3217), *L. crispatus* KS 119.4 (CNCM I-3484), and *L. jensenii* KS 121.1 (CNCM I-3219).

3. The method according to claim 1, wherein the at least one probiotic strain is administered in combination with a delivery system that keeps intact all the properties of the at least one probiotic strain.

4. The method according to claim 1, wherein the probiotic composition is administered in combination with a support or carrier.

5. The method according to claim 4, wherein the support or carrier is designed for local administration, selected from the group consisting of intra-urethral, vaginal and anal administration.

6. The method according to claim 4 wherein the support or carrier is designed for oral administration.

7. The method according to claim 6 wherein the support or carrier is a food product or a beverage, a food or beverage composition, a food or beverage supplement or adjuvant dedicated to human consumption.

8. The method according to claim 1, wherein the probiotic composition further comprises lactic acid bacteria (LAB) growth factors and/or prebiotic ingredients.

9. The method according to claim 8, wherein the lactic acid bacteria (LAB) growth factors and/or prebiotic ingredients is/are selected from the group consisting of skim milk powder (MSK), pH stabilizers, viscosity stabilizers, preservatives, antioxidants, colorants, flavors and one or more sugar(s) that match sugar metabolism profiles of the at least one probiotic strain.

10. A method of treating a urogenital infection in a female or a gastrointestinal dysbiosis and/or infection in a human comprising administering to said female or said human a probiotic composition comprising an effective amount of at least one probiotic strain of the genus *L. crispatus, L. gasseri, L. helveticus* and *L. jensenii* selected from the group consisting of *L. crispatus* KS 116.1 (CNCM I-3483), *L. crispatus* KS 119.4 (CNCM 1-3484), *L. crispatus* 127.1 (CNCM 1-3486), *L. gasseri* KS 114.1 (CNCM 1-3482), *L. gasseri* KS 120.1 (CNCM 1-3218), *L. gasseri* KS 123.1 (CNCM I-3485), *L. gasseri* KS 124.3 (CNCM 1-3220), *L. helveticus* KS 300 (CNCM 1-3360), *L. jensenii* KS 119.1 (CNCM 1-3217) and *L. jensenii* KS 121.1 (CNCM 1-3219).

11. The method of claim 10, wherein the probiotic composition comprises a mixture of *Lactobacillus* strains, the mixture comprising *L. gasseri* KS 120.1 (CNCM 1-3218) in combination with at least one of *L. jensenii* KS 119.1 (CNCM I-3217), *L. crispatus* KS 119.4 (CNCM I-3484), and *L. jensenii* KS 121.1 (CNCM I-3219).

12. The method according to claim 10, wherein the at least one probiotic strain is administered in combination with a delivery system that keeps intact all the properties of the at least one probiotic strain.

13. The method according to claim 10, wherein the probiotic composition is administered in combination with a support or carrier.

14. The method according to claim 13, wherein the support or carrier is designed for local administration, selected from the group consisting of intra-urethral, vaginal and anal administration.

15. The method according to claim 13 wherein the support or carrier is designed for oral administration.

16. The method according to claim 15 wherein the support or carrier is a food product or a beverage, a food or beverage composition, a food or beverage supplement or adjuvant dedicated to human consumption.

17. The method according to claim 10, wherein the probiotic composition further comprises lactic acid bacteria (LAB) growth factors and/or prebiotic ingredients.

18. The method according to claim 17, wherein the lactic acid bacteria (LAB) growth factors and/or prebiotic ingredients is/are selected from the group consisting of skim milk powder (MSK), pH stabilizers, viscosity stabilizers, preservatives, antioxidants, colorants, flavors and one or more sugar(s) that match sugar metabolism profiles of the at least one probiotic strain.

19. A method of treating an inflammatory syndrome, an infectious syndrome or a neoplasic process in a human comprising administering to said human a probiotic composition comprising an effective amount of at least one probiotic strain of the genus *L. crispatus, L. gasseri, L. helveticus* and *L. jensenii* selected from the group consisting of *L. crispatus* KS 116.1 (CNCM I-3483), *L. crispatus* KS 119.4 (CNCM 1-3484), *L. crispatus* 127.1 (CNCM 1-3486), *L. gasseri* KS 114.1 (CNCM 1-3482), *L. gasseri* KS 120.1 (CNCM 1-3218), *L. gasseri* KS 123.1 (CNCM I-3485), *L. gasseri* KS 124.3 (CNCM 1-3220), *L. helveticus* KS 300 (CNCM 1-3360), *L. jensenii* KS 119.1 (CNCM 1-3217) and *L. jensenii* KS 121.1 (CNCM I-3219).

20. The method of claim 19, wherein the probiotic composition comprises a mixture of *Lactobacillus* strains, the mixture comprising *L. gasseri* KS 120.1 (CNCM 1-3218) in combination with at least one of *L. jensenii* KS 119.1 (CNCM I-3217), *L. crispatus* KS 119.4 (CNCM I-3484), and *L. jensenii* KS 121.1 (CNCM I-3219).

21. The method according to claim 19, wherein the at least one probiotic strain is administered in combination with a delivery system that keeps intact all the properties of the at least one probiotic strain.

22. The method according to claim 19, wherein the probiotic composition is administered in combination with a support or carrier.

23. The method according to claim 22, wherein the support or carrier is designed for local administration, selected from the group consisting of intra-urethral, vaginal and anal administration.

24. The method according to claim 22 wherein the support or carrier is designed for oral administration.

25. The method according to claim 24 wherein the support or carrier is a food product or a beverage, a food or beverage composition, a food or beverage supplement or adjuvant dedicated to human consumption.

26. The method according to claim 19, wherein the probiotic composition further comprises lactic acid bacteria (LAB) growth factors and/or prebiotic ingredients.

27. The method according to claim 26, wherein the lactic acid bacteria (LAB) growth factors and/or prebiotic ingredients is/are selected from the group consisting of skim milk powder (MSK), pH stabilizers, viscosity stabilizers, preservatives, antioxidants, colorants, flavors and one or more sugar(s) that match sugar metabolism profiles of the at least one probiotic strain.

\* \* \* \* \*

UNITED STATES PATENT AND TRADEMARK OFFICE
CERTIFICATE OF CORRECTION

PATENT NO. : 10,213,466 B2
APPLICATION NO. : 15/291880
DATED : February 26, 2019
INVENTOR(S) : Federico Graf et al.

It is certified that error appears in the above-identified patent and that said Letters Patent is hereby corrected as shown below:

On the Title Page

Item (71), change "Beckenreid" to --Beckenried--.

Item (72), first inventor, change "Beckenreid" to --Beckenried--.

In the Specification

Column 1, Line 47, change "Doederlein" to --Doderlein--.

Column 2, Line 14 (approx.), change "Dec. 10, 2004" to --Oct. 22, 2004--.

Column 3, Line 17, change "as" to --.--.

Column 3, Line 43 (approx.), change "3260" to --3360--.

Column 4, Line 30, change "Typmmurium," to --Typhimurium,--.

Column 5, Line 21, change "DFUC5" to --DFUC5,--.

Column 5, Line 22, change "LFUC5" to --LFUC5,--.

Column 6, Line 35, change "MAL" to --MAL,--.

Column 7, Line 14, after "treatments" insert --.--.

Column 7, Line 19, change "(MSK)" to --(SMP).--.

Column 7, Line 61 (approx.), change "Srain" to --Strain--.

Signed and Sealed this
Sixteenth Day of July, 2019

Andrei Iancu
*Director of the United States Patent and Trademark Office*

CERTIFICATE OF CORRECTION (continued)

Column 7, Line 62 (approx.), change "hensenii" to --jensenii--.

Column 8, Line 26, change "Galvestone)" to --Galveston)--.

Column 8, Line 35, change "370 C" to --37° C.--.

Column 8, Line 44, change "370 C" to --37° C.--.

Column 8, Line 54, change "370 C" to --37° C.--.

Column 9, Line 8-9 (approx.), change "(Invitrogene)" to --(Invitrogen)--.

Column 9, Line 9 (approx.), change "(Invitrogene)" to --(Invitrogen)--.

Column 10, Line 41, change "KS 116A" to --KS 116.1--.

Column 11, Line 61, change "and and" to --and--.

Column 13, Line 30 (approx.), change "that that" to --that--.

Column 14, Line 15, change "Gardneralla" to --Gardnerella--.

Column 14, Line 40, change "Eschrichia" to --Escherichia--.

Column 15, Line 18, change "*L. crispatus* KS 120.1" to --*L. gasseri* KS 120.1--.

Column 15, Line 56, change "*L. crispatus* KS 120.1" to --*L. gasseri* KS 120.1--.

Column 15, Line 58, change "*L. crispatus* KS 120.1" to --*L. gasseri* KS 120.1--.

Column 15, Line 32 (approx.), after "buffer" insert --.--.

Column 15, Line 63 (approx.), change "PMBC)" to --PBMC)--.

Column 16, Line 14 (approx.), change "PMBC" to --PBMC--.

Column 16, Line 19, change "monocular" to --mononuclear--.

Column 16, Line 19, change "(PMBC's)" to --(PBMC's)--.

Column 16, Line 20, change "PMBC's" to --PBMC's--.

Column 16, Line 24, change "PMBC's" to --PBMC's--.

Column 16, Line 25, change "(GIBCOP),m" to --(GIBCO)--.

CERTIFICATE OF CORRECTION (continued)
U.S. Pat. No. 10,213,466 B2

Column 16, Line 35, change "PMBC" to --PBMC--.

Column 16, Line 36, change "PMBC" to --PBMC--.

Column 16, Line 49 (approx.), change "streptavidine" to --streptavidin--.

Column 16, Line 50 (approx.), change "Pharmigen)." to --Pharmingen).--.

Column 16, Line 50 (approx.), change "Pharmigen" to --Pharmingen--.

In the Claims

Column 18, Line 67, in Claim 9, change "(MSK)" to --(SMP)--.

Column 19, Line 46, in Claim 18, change "(MSK)" to --(SMP)--.

Column 20, Line 45, in Claim 27, change "(MSK)" to --(SMP)--.